United States Patent [19]

Ben-Michael

[11] Patent Number: 4,886,760
[45] Date of Patent: Dec. 12, 1989

[54] STABLE CHEMICAL COMPOSITIONS CONTAINING CHROMOGENIC MATERIALS, PEROXIDES, AND STABILIZING CHEMICALS

[75] Inventor: Abraham Ben-Michael, Ramat-Ilan, Israel

[73] Assignee: Savyon Diagnostics Limited, Israel

[21] Appl. No.: 891,528

[22] Filed: Jul. 31, 1986

Related U.S. Application Data

[63] Continuation-in-part of Ser. No. 771,417, Aug. 30, 1985, abandoned.

[30] Foreign Application Priority Data

Jan. 31, 1985 [IL] Israel ........................................ 74204
Dec. 11, 1985 [IL] Israel ........................................ 77299

[51] Int. Cl.$^4$ .............................................. G01N 21/78
[52] U.S. Cl. ........................................ 436/66; 435/28; 436/164; 436/904
[58] Field of Search .................. 436/66, 135, 164, 166, 436/74, 127, 136, 138, 904; 435/28, 27; 252/186.22, 186.25, 186.26, 186.28, 186.38, 186.41, 186.42, 186.43

[56] References Cited

U.S. PATENT DOCUMENTS

| | | | |
|---|---|---|---|
| 3,630,847 | 12/1971 | Rey et al. | 436/66 X |
| 3,753,863 | 8/1973 | Speck | 435/14 |
| 3,917,452 | 11/1975 | Rittersdorf et al. | 436/66 |
| 4,017,261 | 4/1977 | Svoboda et al. | 435/28 X |
| 4,077,772 | 3/1978 | Geissler et al. | 436/904 X |
| 4,120,652 | 10/1978 | Scholer et al. | 252/186.22 X |
| 4,143,080 | 3/1979 | Harders et al. | 436/66 |
| 4,320,102 | 3/1982 | Dalton, Jr. et al. | 252/186.28 X |
| 4,331,761 | 5/1982 | Dawson et al. | 435/28 X |
| 4,339,242 | 7/1982 | Magers et al. | 435/28 X |
| 4,447,542 | 5/1984 | Gantzer | 436/66 |
| 4,556,640 | 12/1985 | Gantzer | 436/66 |
| 4,596,770 | 6/1986 | Parham et al. | 435/7 |
| 4,615,982 | 10/1986 | Lawrence | 422/56 X |

FOREIGN PATENT DOCUMENTS

| | | |
|---|---|---|
| 0121317 | 10/1984 | European Pat. Off. |
| 0222766 | 12/1984 | Japan ........................................ 436/66 |
| 8001972 | 11/1981 | Netherlands . |

OTHER PUBLICATIONS

Rider et al, J.A.M.A., vol. 156, pp. 31–33, 1954.
Baskin et al, *J. Histochem. and Cytochem.*, 30 (7), 710–712 (1982).
A. G. E. Pearse, *Histochemistry–Theoretical and Applied*, p. 230, vol. 1 (1980).
*Diagnostic Procedures for Viral, Rickettsial and Chlamydial Infections* (1979), p. 160.
Liem et al, *Anal. Biochem.*, 98, 338–393 (1979).
Levinson and Goldman, *Clin. Chem.*, 28/3, 471–474 (1981).
Kaplow, L. S., *A. J. Chem. Pathol.*, 63, 451 (1975).

*Primary Examiner*—Robert J. Hill, Jr.
*Attorney, Agent, or Firm*—Lerner, David, Littenberg, Krumholz & Mentlik

[57] ABSTRACT

It is known that chromogenic materials which yield a color reaction when in the presence of a peroxide of the formula ROOR' which decomposes to yield ROR' and oxygen are unstable when in the form of working solutions for use in chromogenic reactions. Such compositions which also contain the peroxide required for such reactions are also unstable, leading to premature appearance of color. Stable chemical compositions are disclosed herein containing chromogenic materials and containing mixtures of chromogenic materials and peroxides, which can be used in chromogenic reactions after having been stored for long periods of time. Stabilizing chemical compositions and methods are also disclosed for obtaining such stable compositions.

14 Claims, No Drawings

STABLE CHEMICAL COMPOSITIONS CONTAINING CHROMOGENIC MATERIALS, PEROXIDES, AND STABILIZING CHEMICALS

CROSS-REFERENCE TO RELATED APPLICATIONS

This application is a continuation-in-part of pending U.S. patent application Ser. No. 771,417, filed on Aug. 30, 1985, now abandoned.

FIELD OF THE INVENTION

The present invention relates to methods for obtaining stable chemical compositions containing chromogenic materials. More particularly, the present invention relates to stabilizing chemical compositions to be used for obtaining stable chemical compositions containing chromogenic materials. Still more particularly, the presennt invention relates to methods for obtaining stable chemical compositions containing mixtures of chromogen materials and peroxides. More particularly, the present invention relates to stabilizing chemical compositions to be used for obtaining stable chemical compositions containing mixtures of chromogen materials and peroxides, as well as to the stable chemical compositions obtained thereby.

BACKGROUND OF THE INVENTION

Throughout this specification, a chromogen material is defined as a material which changes its color when in the presence of a peroxide of the formula ROOR' which decompose to yield ROR' and oxygen. R and R' are defined as being each independently hydrogen or an organic substituent which can suitably form an organic peroxide.

Chromogen materials are of importance in a large variety of chemical and clinical tests, and are commonly employed in a wide number of practical applications, e.g. for qualitative or even quantitative tests.

ROOR' causes the change in color of the chromogen material when it is decomposed and yields a radical oxygen according to the reaction:

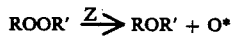

in which Z may be any agent which causes this decomposition reaction to take place, for example: UV light, metal ions, active enzymes like peroxidase or catalase, etc., or a pseudo-peroxidase like hemoglobin or Cytochrom-C.

Since, however, the decomposition of ROOR' takes place quite easily, and since the color reaction must only take place at the desired time and under controlled conditions, the art has accepted as unavoidable the requirement that such chromogen solutions cannot be stored for long periods of time, but must be normally freshly prepared before each use. This problem is even more severe when it is desired to prepare chromogen solutions which already contain the desired peroxide. Even in those instances where there has been some success in obtaining such solutions which can be stored for short periods of time, severe limitations must be imposed on the storage thereof or on their use (e.g. use is thus sometimes forbidden in direct sunlight).

There are some prior examples of such solutions involving chromogenic products and their use. These include Liem et al (Anal. Biochem. 98, 338–393 (1979)) who report the use of 3,3',5,5'-Tetramethylbenzidine dihydrochloride for the quantitative determination of hemoglobin. Hydrogen peroxide is converted to water and oxygen by peroxidase. Tetramethylbenzidine dihydrochloride in water or acetic acid is mixed with a water solution of freshly prepared hydrogen peroxide. This solution, if stored in the refrigerator, can be used for several days.

Also, Levinson and Goldman (Clin. Chem. 28/3. 471–474 (1981)) used a TMB solution in water/acetic acid for measuring hemoglobin in plasma. The working solution containing hydrogen peroxide was stable at room temperature for 4 hours.

Other examples of such solutions which are to be freshly prepared before use according to the art are those based on 3-amino-9-ethylcarbazole (Kaplow, L. S., A. J. Chem. Pathol. 63, 451, 1975), and 4-chloro-1-naphthol, for electrion microscopic immunoperoxidase staining of insulin (Baskin et al, J. Histochem. and Cytochem., 30 (7) 710–712 (1982)), (A. G. E. Pearse, Histochemistry-Theoretical and Applied, p. 230, vol. 1 (1980)).

In one instance (Diagnostic Procedures for Viral, Rickettsial and Chlamydial Infections (1979), p. 160) it is reported that a solution of benzidine dihydrochloride is obtained which is stable in the presence of hydrogen peroxide for approximately 3 months.

There are also a large number of commercially available reagents and kits, employing chromogenic/hydrogen peroxide action, all of which are subject to strict limitations.

These include a Beta Specific Monoclonal Enzyme Linked Immunosorbent Assay for Pregnancy manufactured by Roche. The chromogen reagent employed there is tetramethylbenzidine in methanol, and the conjugate reagent is peroxidase. In this case, the manufacturer directs the user to keep all reagents tightly closed and upright, and not to store reagents in direct sunlight during use. The reagents are then mixed immediately before use.

A kit for the Quantitative Immunoenzyme Determination of IgG Antibodies to Rubella Virus in Serum or Plasma Samples is manufactured by Sorin/Biomedica, and employs two constituents of the reagent: (1) $H_2O_2$ in phosphate-citrate buffer at pH 5.15, and (2) merthiolate and ortho-phenylenediamine.2HCL lyophilized. The reagent obtained by mixing these two components must then be used within 15 to 30 min., and should be sheltered from intense light.

In the 1983 DAKOPATTS price list there are found three chromogens for peroxidase staining, namely diaminobenzidine (DAB), orthophenylenediamine (oPD) and 3-amino-9-ethylcarbazole (AEC). It is specified that stock solutions of DAB and oPD should be kept at $-20°$ C., and AEC at $4°$ to $8°$ C. Again, hydrogen peroxide should not be added until shortly before use.

The instructions for preparing HRP color development solution for use in Bio-Rad's Immun-Blot assay system provide for the addition of ice cold $H_2O_2$ immediately prior to use.

The immunoperoxidase staining kit for human antigens, manufactured by Lerner Laboratories, employs 3-amino-9-ethylcarbazole as the chromogen. $H_2O_2$ and the reagent are added stepwise during testing.

Although chromogenic reagents are thus widely used for a large number of applications, the art has not yet succeeded in providing a method for obtaining peroxide/chromogen-containing solutions which are stable for long periods of time, and which do not require strict storage and handling limitations. Furthermore, even in the absence of a peroxide, chromogen solutions are often unstable. These facts have limited the use and application of chromogenic techniques.

SUMMARY OF THE INVENTION

It is therefore an object of the present invention to provide methods and stabilizing chemical compositions for obtaining stable chemical compositions containing chromogen materials.

It is a further object of the present invention to provide methods and stabilizing chemical compositions for obtaining stable chemical compositions containing mixtures of chromogenic materials and peroxides.

It is still another object of the present invention to provide stable chemical compositions containing chromogen materials and stable chemical compositions containing mixtures of chromogenic materials and peroxides.

The exact nature of the chromogen employed in connection with the present invention is not essential, although different chromogens may exhibit stability for different periods of time. All of these chromogens, however, will exhibit long-term and improved stability when stabilized according to this invention. Examples of fully soluble and partially precipitating chromogens are: o-dianizidine, o-toluidine, 5-amino salicyclic acid, chloronaphthol, benzidine, tetramethylbenzidine, 3-amino-9-ethylcarbazole, dichloronaphthol, dibromonaphthol, 3,3',5,5'-tetramethylbenzidine dihydrochloride, 3,3',5,5'-tetramethylbenzidine (dihydrochloride dihydrate), 3-methylbenzothiazole-2,1-hydrazone, parahydroxyphenyl acetic acid, 2,2'-amino-di (3-ethylbenzothiazoline sulfonic acid), guaiacol, o-tolidine and pyrogallol.

Examples of inorganic and organic peroxides are, e.g. $H_2O_2$ and Cumene hydroperoxide ($C_6H_5C(CH_3)_2$ OOH). It has also been found, however, that the stable chromogen-containing compositions of the present invention can include organic peroxides, (ROOR') such as Cumene hydroperoxide, 2-butanone peroxide and tert-butyl-hydroperoxide, particularly with some preferred, particularly stable chromogencontaining compositions hereof.

The present invention can also be usefully exploited in self-generating systems, i.e. solutions in which the peroxide needed for the chromogenic reaction is generated "in situ", instead of being externally added as is done, for example, in the above mentioned kits.

In accordance with the present invention, stable chromogen-containing compositions have now been discovered comprising an aqueous solvent medium, a chromogenic material, a water miscible organic solvent, a stabilizing compound comprising at least two unsaturations and at least one cyclic moiety, and an effective amount of a chelating agent to stabilize these chromogencontaining compositions in the liquid state. Preferably, the water miscible organic solvent has a gas-phase dipole moment of at least about 1.60 D, and most preferably at least about 1.69 D. In a preferred embodiment, the water miscible organic solvent is an aprotic solvent.

According to a preferred embodiment of the present invention, the aqueous solvent medium comprises a buffer solution.

In connection with the stabilizing compounds of this invention, by unsaturation is meant ethylenic double bonds or aromatic or heteroaromatic unsaturations.

According to a preferred embodiment of the invention, the unsaturations in the stabilizing compound are included in the cyclic moiety. According to this embodiment, therefore, ethylenic unsaturations may not be present, and the stabilizing compound comprising at least two unsaturations and at least one cyclic moiety may be a cyclic compound, e.g. a substituted benzene ring.

According to a preferred embodiment of the present invention, the stabilizing compound comprises an unsaturated nitrogen heterocyclic compound. These compounds have thus been found to be particularly useful as such stabilizing compounds.

According to a preferred embodiment of the present invention, the compound comprising at least two unsaturations and at least one cyclic moiety is selected from among:

a compound of the general formula:

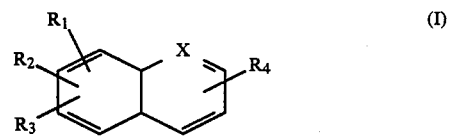

(I)

wherein each of $R_1$, $R_2$, $R_3$ and $R_4$ may be independently hydrogen, hydroxy, $CF_3$, halogen, nitro, $SO_2OH$, $NHCH_2CH_2NH_2$ or lower alkyl, and X is nitrogen, oxygen, carbon or sulfur;

or a compound of the formula:

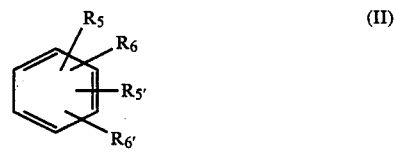

(II)

in which $R_5$, $R_{5'}$, $R_6$ and $R_{6'}$ may each be hydrogen, lower alkenyl, $-NH_2$, phenyl optionally substituted, $-NO_2$, halogen, $-OCH_3$, hydroxy, $COOC_6H_5$, COOH, $CH_2COOH$ or $SO_2OH$;

or a compound of the formula:

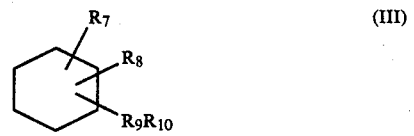

(III)

in which $R_7$ and $R_8$ may each be hydroxy or lower alkenyl, $R_9$ is alkenyl, and $R_{10}$ is an azulene group optionally substituted by one or more straight or branched alkyl group of $C_1$-$C_{10}$;

or a compound of the formula:

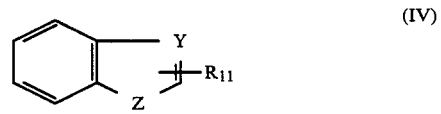

(IV)

wherein Y and Z may each be oxygen, nitrogen or sulfur, and $R_{11}$ is hydrogen or hydroxyphenyl;

or a compound of the formula:

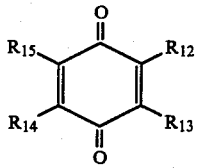

(V)

wherein each of $R_{12}$, $R_{13}$, $R_{14}$ and $R_{15}$ may independently be hydrogen, hydroxy or lower alkyl;
or a compound of the formula:

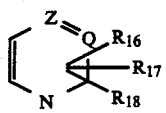

(VI)

wherein each of Z and Q is either C or N, but both of Z and Q are not N, and in which $R_{16}$, $R_{17}$, and $R_{18}$ may independently be hydrogen, hydroxy, —NH, alkyl, preferably lower alkyl, amino, —$SO_3H$, —$CO_2H$, benzo or piperidino;
or a salt of one of compounds of formula (I), (II), (III), (IV), (V), or (VI).

The aqueous solvent medium further preferably contains from 0 to about 5000 ppm, and preferably from 0 to about 2400 ppm of a chelating agent or agents. These chelating agents are preferably selected from pyrophosphate, acetanilide, citrate, nitrilotriacetic acid, or a derivative of 8-hydroxyquinoline, either alone or in admixture of two or more such chelating agents.

A preferred composition according to the present invention contains: from 0 to about 200 ppm pyrophosphate, from 0 to about 200 ppm acetanilide, from 0 to about 1000 ppm citrate, from 0 to about 200 ppm 8-hydroxyquinoline or a salt thereof.

The water miscible organic solvent hereof is preferably selected from methanol, ethanol, dimethylsulfoxide, sulfolane, acetamide, soluted dimethylsulfone, hexamethylphosphoric triamide, N-methylacetamide, dioxane, dimethylformamide, soluted trioxane, formamide or tetrahydrofuran.

The stabilizing compound of formula (I) is preferably selected from among 8-hydroxyquinoline, 4-chloro-7-(trifluoromethyl) quinoline, 5-chloro-7-iodo-8-hydroxyquinoline, 5-chloro-8-hydroxyquinoline or a copper or hemi-sulfate salt of 8-hydroxyquinoline. The stabilizing compound of formula (II) is preferably aniline 2-sulfonic acid, and the stabilizing compound of formula (III) is preferably Colecalciferol. Furthermore, the stabilizing compound of formula (VI) is preferably selected from among 2-amino-4,6-dimethylpyridine, 2-amino-4,6-dimethylpyrimidine, 2-amino-6-methyl pyridine, 2,4,6-collidine, 3-(aminomethyl) pyridine, 2-quinoxalinol, 4-amino-2,6-dimethylpyridine, 5-ethyl-2-methylpyridine, 4-methylpyrimidine, 2,6-lutidin, ethyl nicotinate, 4-piperidnopyridine, 2-aminoethylpyridine, 4-pyridinecarboxylic acid, pyridine-3-sulfonic acid and purine.

When the aqueous solvent medium is a buffer solution, the buffer is preferably selected from among: phosphate buffer (PB), Tris buffer (hydroxymethylaminomethane), borate buffer, glycine buffer and acetate buffer.

It has also been found in accordance with a preferred embodiment of the present invention that it is now possible to obtain stable solutions of chromogenic materials, having a very low (down to about 2) or a very high (up to about 11) pH. Most particularly, these stable chromogen-containing compositions can have a pH of between about 2 and 5, or a pH of between about 7 and 11.

In accordance with the stable chemical compositions of the present invention, these comprise an aqueous solvent medium, or a buffer solution, from 0 to about 5000 ppm of a chelating agent, a water miscible organic solvent, preferably having a gas-phase dipole moment equal to or greater than 1.60 D, and most preferably greater than 1.69 D, a stabilizing compound comprising at least two unsaturations and at least one cyclic moiety, and a chromogenic material.

The chromogen materials is preferably selected from the group comprising: chloronaphthol, benzidine, tetramethylbenzidine, 3-amino-9-ethylcarbazole, dichloronaphthol, dibromonaphthol, 3,3',5,5'-tetramethylbenzidine dihydrochloride, 3,3',5,5'-tetramethylbenzidine (dihydrochloride dihydrate), 3-methylbenzothiazole-2,1-hydrazone, parahydroxyphenyl acetic acid, 2,2'-azino-di(3-ethylbenzothiazoline) sulfonic acid, 4-aminoantipyrin/alphanaphthol, o-dianizidine, o-toluidine, 5-amino salicylic acid, guaiacol, o-tolidine and pryogallol.

The stable chromogen-containing compositions according to the present invention may further contain one or more peroxides.

According to a preferred embodiment of this invention the peroxide is hydrogen peroxide.

According to another preferred embodiment of this invention, the peroxide is an organic hydroperoxide, more preferably Cumene hydroperoxide, or an organic peroxide such as tert-butylhydroperoxide or 2-butanone peroxide.

The method for obtaining the stable chromagen-containing compositions according to this invention comprises carrying out, in any convenient order, the steps of:

a. preparing an aqueous solvent medium, preferably having a pH of from about 5 to 8, and containing an effective amount of a chelating agent to stabilize the composition, e.g., from 0 up to about 5000 ppm, b. preparing a chromogen solution in a water miscible organic solvent in the presence of a stabilizing compound comprising at least two unsaturations and at least one cyclic moiety, c. mixing solutions (a) and (b) together; and d. adding an alkaline or acidic solution to obtain the desired final pH.

The method for obtaining the stable chemical compositions of the present invention which further contain a peroxide comprises carrying out, in any convenient order, the steps of:

a. preparing an aqueous solvent medium having a pH of from about 5 to 8, and containing from 0 to about 5000 ppm of a chelating agent, b. preparing a chromogen solution in a water miscible organic solvent in the presence of a stabilizing compound comprising at least two unsaturations and at least one cyclic moiety, c. mixing solutions (a) and (b) together, d. adding an alkaline or acidic solution to obtain the desired final pH, and e. adding the desired peroxide.

It should also be noted that in accordance with the prior art, peroxides are very sensitive to and easily decomposed by dirt and organic materials. All of the numerous compositions which were thus prepared according to this invention were therefore tested for stability under "dirt conditions" by the introduction of dust. None of the tested compositions lost stability, however, even under such conditions.

The addition of chelating agents is rendered necessary by the presence of ions such as $Al^{+++}$, $Ni^{++}$, $Mg^{++}$, $Ca^{++}$, $Hg^+$ and $Hg^{++}$, which are commonly present either in the water-if not highly purified-or in the glass vessels employed. These ions catalyze decomposition of the peroxide. In the event, however, that total absence of such ions can be obtained, the chelating agents can be dispensed with.

It should be noted that, while the crucial requirement for the organic solvent is its dipole moment, it will be readily understood by a person or ordinary skill in this art that sufficient solubility of a specific chromogen in a chosen organic solvent is essential, and that chromogen/solvent pairs may exist which are incompatible for practical purposes.

It should be further noted that the pH of the stabilized solution may vary over a wide range, without resulting in a sensible destabilization thereof. The desired pH is primarily dictated by the optimal conditions for the dissolution of the chromogen in the organic solvent, and for the activity of the $ROOR^1$ decomposing agent.

The aforesaid and other characteristics and advantages of this invention will be better understood through the following illustrative and non-limitative examples thereof. Stability is checked in the examples by reaction with peroxidase or a pseudoperoxidase, and development of color. Examples 112–121 refer to the preparation of 100 ml of solution.

EXAMPLE 1

Preparation of stable solution containing 4-chloro-1-naphthol.

1. Preparation of solution A 500 mg of 4-chloro-1-naphthol and 1000 mg of 8-hydroxyquinoline-hemi-sulphate salt were dissolved in 200 ml of dimethylsulfoxide (dipole moment 3.96 D).

2. Preparation of solution B

To 800 ml of distilled water there was added 968 mg of Tris buffer, 80 mg of acetanilide, 80 mg of pyrophosphate and 800 mg of citrate.

3. Preparation of final solution

Solution A was slowly added to solution B with stirring. The resulting solution was titrated with 10N NaOH until a pH of 7.6 was obtained. The solution was allowed to cool to about ambient temperature and thereafter 500 microliters of $H_2O_2$ were added. 1000 mls of solution was obtained. This solution was stable on the desk for 12 months.

EXAMPLES 2 THROUGH 105

Several compositions according to the invention were prepared and tested for stability in the so-called "shelf-life test". In this test the composition was kept at three different temperatures: 4°, 25° and 37° C. The compositions were kept in brown amber glass bottles with plastic caps. Destabilization was determined by color development, and activity by color development on slide in the presence of a peroxidase. The results of these tests are summarized in Table VI.

The various symbols, abbreviations and ranges of the materials used in Table VI are explained in Tables I to V. Tables I to V are for the purpose of exemplifying several preferred aqueous and organic solvents, chelating agents and compounds containing at least two unsaturations and at least one cyclic moiety (hereinafter referred to as "TuOcm" compounds) is being understood, however, that these tables are not intended to be limitative.

The following are the detailed meanings of the column headings in Table VI:

n-composition number
Aq. Solv.-Aqueous solvent employed
Chel.-chelating agent(s) employed
Org. Solv.-organic solvent employed
Compd.-TuOcm compound employed
Chr.-chromogen material employed
pH rg.-range of pH employed
shelf life-minimal stability of composition (in months) for the appropriate temperature.

As a stable composition is meant a composition which reacts to give the desired color reaction.

Tests have been carried out using hydrogen peroxide as the test peroxide, unless otherwise indicated.

TABLE I

| | Aqueous Solvents | | |
|---|---|---|---|
| Symbol | Solvent | pH Range | Molarity Range |
| BB | Borate Buffer | 7.5–8.5 | 0.001–0.05 M |
| TB | Tris Buffer | 6.8–7.6 | 0.001–0.05 M |
| PB | Phosphate Buffer | 6.8–7.6 | 0.001–0.05 M |
| AB | Acetate Buffer | 5.0–6.0 | 0.001–0.05 M |
| DW | Distilled or Deionized Water | 6.8–7.6 5.0–6.0 | — |
| TW | Tap Water | 6.8–7.6 5.0–6.0 | — |

TABLE II

| | Organic Solvents |
|---|---|
| Symbol | Solvent |
| DMSO | Dimethylsulfoxide |
| DMSO2 | Dimethylsulfone[b] |
| TMS | Tetramethylensulfone (Sulfolane) |
| DMF | N,N—Dimethylformamide |
| DMAC | N,N—Dimethylacetamide |
| MetOH | Methanol |
| EtOH | Ethanol[c] |
| MAM | N—Methylacetamide |
| ACA | Acetamide |
| DXA | Dioxane |
| TXA | Trioxane[b] |
| FMA | Formamide |
| THF | Tetrahydrofuran |
| MAC | N—Methylacrylamide |

[b]Melted or water soluted
[c]Dipole moment 1.69 D.

TABLE III

| | Chelating agents | |
|---|---|---|
| Symbol | Substance | Concentration range (ppm) |
| A | Acetanilide | 0–200 |
| P | Sodium pyrophosphate decahydrate | 0–200 |
| C | citric acid, tri sodium salt | 0–1000 |
| 8HQ | 8-Hydroxyquinoline | 0–2000 |
| NAA | Nitrilotriacetic acid | 0–200 |

TABLE IV

TuOcm Compounds

| Symbol | Substance |
|---|---|
| DNS | 2,4-Dinitro-1-naphthol-7-sulfonic acid |
| DN | 2,4-Dinitro-1-naphthol |
| NE | N—1-naphthyl-ethylenediamine |
| NP | 4-nitro-o-phenylenediamine |
| CI8HQ | 5-chloro-7-iodo-8-hydroxyquinoline |
| C8HQ | 5-chloro-8-hydroxyquinoline |
| CC | colecalciferol (Vitamin $D_3$) |
| DP | 2,4-Dinitrophenol |
| TP | Trinitrophenol |
| NPD | 2-Nitro-p-phenylenediamine |
| COP | 4-chloro-O-phenylenediamine |
| HPB | 2-(2-hydroxyphenyl) benzoxazole |
| HBH | 1-Hydroxybenzothiazole hydrate |
| MP | 2-Methoxyphenol (Guaiacol) |
| 8HQ | 8-hydroxyquinoline |
| 8HQ HS | 8-hydroxyquinoline hemi-sulfate salt |
| THQ | Tetrahydroxy-1,4-quinone |
| CTQ | 4-chloro-7-(Trifluoromethyl)quinoline |
| CTA | 2-(2-chloro-1,1,2-trifluoroethylthio)aniline |
| PT | p-Toluidine |
| OT | o-Toluidine |
| DHN | 1,2-di-hydroxy naphthalene |
| PS | Phenyl-salicylate |
| HABA | 2-(4'-hydroxyazobenzene)benzoic acid |
| AS | aniline 2-sulfonic acid |
| NQ | 1,4-Naphthoquinone |
| TMB | N,N,N',N'—Tetramethylbenzidine |
| HDPH | o-Hydroxydiphenyl |
| PQD | Primaquine diphosphate |
| QT | Quercetin |
| SDZ | Sodium diatrizoate |
| VAA | Vanillic acid |
| VA | Vanilline |
| THM | Thymol |
| TBP | 2,4,4'-Trihydroxybenzophenone |
| HBP | 2-Hydroxybenzophenone |
| AIQ | 5-Aminoisoquinoline |
| BMA | N—Benzylidenemethylamine |
| BBA | N—Benzylidenebenzylamine |
| BA | 10-Benzylidene-9-anthrone |
| GSA | Guaiacol sulfonic acid |
| AP | 2-Aminopyridine |
| APM | 2-Aminopyrimidine |
| AHHP | 2-Amino-4-hydroxy-6-hydroxypyrazole-[3,4-d]pyrimidine |
| DAA | 4-Dimethylaminoantipyrine |
| DPP | 3,4-Dimethyl-1-phenyl-3-pyrazolin-5-one |
| DPD | 2,2'-Dipyridyl |
| BHA | o-Benzylhydroxylamine.HCl |
| MY | Martius Yellow |
| FA | Flavianic acid |

$(a)$concentration range: 0–2000 ppm

TABLE V

$(a)$Chromogens

| Symbol | Substance |
|---|---|
| CN | 4-chloro-1-naphthol |
| DCN | 2,4-Dichloro-1-naphthol |
| BZ | Benzidine.2HCl |
| DMB | 3,3'-Diaminobenzidine.4HCl |
| TMB | 3,3',5,5'-Tetramethylbenzidine |
| TMBd | 3,3',5,5'-Tetramethylbenzidine.2HCl |
| TMBd.2H2O | 3,3',5,5'-Tetramethylbenzidine.2HCl.2H$_2$O |
| AEC | 3-Amino-9-Ethylcarbazole |
| HPAA | p-Hydroxyphenylacetic acid |
| OTI | o-Tolidine |
| OD | o-Dianisidine |
| G | 2-methoxyphenol (Guaiacol) |
| AAP/N | 4-Aminoantipyrine/alpha-naphthol |
| ABTS | 2,2'-Azino-di-(3-ethylbenzthiazoline sulfonic acid) |
| MTH | 3-Methylbenzo - Thiazol-2,1-hydrazone |
| RT | Rutin |
| 5DAB | 3,5-Diaminobenzoic acid |
| 4DAB | 3,4-Diaminobenzoic acid |
| CT | (+)-Catechin |
| GA | Gallic acid |
| PGA | Propyl gallate |
| PTH | Phenothiazine |
| DBA | 4-Dimethylaminobenzoic acid |
| BNP | 1-Bromo-2-naphthol |
| AN | 8-Amino-2-naphthol |
| ACN | 1-Amino-4-chloronaphthol |
| DPA | Diphenylamine |
| 3NPD | 3-Nitro-1,2-phenylenediamine |
| AAP | 4-Aminoantipyrine |
| 4NPD | 4-Nitro-1,2-phenylenediamine |
| ASA | 5-Aminosalycilic acid |
| PGA | Pyrogallol |
| ANS | 8-Amino-1-naphthol-5-sulfonic acid |
| ADPA | p-Aminodiphenylamine |
| AMD | p-Amino-p-methoxy diphenylamine |
| PDA | 1,2-Phenylenediamine |
| pPD | p-Phenylenediamine |
| oPD | o-Phenylenediamine (free base) |
| oPD.HCl | o-Phenylenediamine.HCl |
| TPH | N,N,N',N'—Tetramethyl-p-phenylenediamine.2HCl |
| SGD | Syringaldazine |
| mPD | m-Phenylenediamine |

$(a)$Concentration range: 0–5000 ppm

TABLE VI

Compositions and Stabiltiy Test

| | | | | | | | Shelf life | | |
|---|---|---|---|---|---|---|---|---|---|
| n. | Ag. Solv. | Chel. | Org. Solv. | Cmpd. | Chr. | pH rg. | 4° | 25° | 37° |
| 1 | TB | A + P + C | DMSO | 8HQ HS | CN | 6.8–7.6 | 12 | 6 | 1 |
| 2 | TB | A + P + C | DMSO2 | DMS | G | 6.8–7.6 | 12 | 6 | 1 |
| 3 | TB | A + P + C +8HQ | TMS | DN | OD | 6.8–7.6 | 12 | 6 | 1 |
| 4 | TB | A + P + C | DMF | NE | AAP | 6.8–7.6 | 3 | 1 | ½ |
| 5 | TB | A + P + C +8HQ | DMAC | NP | ABTS | 6.8–7.6 | 3 | 1 | ½ |
| 6 | PB | A + P + C | DMSO | 8HQ HS | CN | 6.8–7.6 | 12 | 6 | 1 |
| 7 | PB | A + P + NAA +8HQ | DMSO2 | DNS | G | 6.8–7.6 | 12 | 6 | 1 |
| 8 | PB | A + P + C | TMS | DN | OD | 6.8–7.6 | 12 | 6 | 1 |
| 9 | PB | A + P + C | DMF | NE | AAP | 6.8–7.6 | 3 | 1 | ½ |
| 10 | PB | A + P + C | DMAC | NP | ABTS | 6.8–7.6 | 3 | 1 | ½ |
| 11 | PB | A + P +8HQ | DMSO | 8HQ HS | CN | 6.8–7.6 | 12 | 6 | 1 |
| 12 | PB | A + P + C | DMSO2 | DNS | G | 6.8–7.6 | 12 | 6 | 1 |

TABLE VI-continued
Compositions and Stabiltiy Test

| n. | Ag. Solv. | Chel. | Org. Solv. | Cmpd. | Chr. | pH rg. | Shelf life 4° | 25° | 37° |
|---|---|---|---|---|---|---|---|---|---|
| 13 | PB | A + P + C | TMS | DN | OD | 6.8–7.6 | 12 | 6 | 1 |
| 14 | PB | A + P + C | DMF | NE | AAP | 6.8–7.6 | 3 | 1 | ½ |
| 15 | PB | A + P + C | DMAC | NP | ABTS | 6.8–7.6 | 3 | 1 | ½ |
| 16 | TB | A + P + C | DMSO | 8HQ HS | BZ | 6.8–7.6 | 3 | 1 | ½ |
| 17 | TB | A + P + C | DMSO2 | DNS | DMB | 6.8–7.6 | 3 | 1 | ½ |
| 18 | AB | A + C +8HQ | TMS | DN | TMB | 5.0–6.0 | 12 | 6 | 1 |
| 19 | AB | A + P + C | DMF | NE | TMBd | 5.0–6.0 | 3 | 1 | ½ |
| 20 | AB | A + P + C | DMAC | NP | TMBd .2H2O | 5.0–6.0 | 12 | 6 | 1 |
| 21 | DW | A + P + C | DMSO | 8HQ HS | CN | 6.8–7.6 | 12 | 6 | 1 |
| 22 | DW | P + C +8HQ | DMSO2 | DNS | G | 6.8–7.6 | 12 | 6 | 1 |
| 23 | DW | A + P + C | TMS | DN | OD | 6.8–7.6 | 12 | 6 | 1 |
| 24 | DW | A + P + C | DMF | NE | AAP | 6.8–7.6 | 12 | 6 | 1 |
| 25 | DW | A + P + C | DMAC | NP | TMBd | 5.0–6.0 | 12 | 6 | 1 |
| 26 | TW | A + P + C | DMSO | 8HQ HS | CN | 6.8–7.6 | 12 | 6 | 1 |
| 27 | TW | A. + P + C | DMSO2 | DNS | G | 6.8–7.6 | 12 | 6 | 1 |
| 28 | TW | A + P + C | TMS | DN | OD | 6.8–7.6 | 12 | 6 | 1 |
| 29 | TW | A + P + C | DMF | NE | AAP | 6.8–7.6 | 12 | 6 | 1 |
| 30 | TW | A + P + C | DMAC | NP | TMBd | 5.0–6.0 | 12 | 6 | 1 |
| 31 | TB | A + P + C | DMSO | 8HQ HS | ABTS | 6.8–7.6 | 3 | 1 | ½ |
| 32 | TB | A + P + NAA | DMSO2 | DNS | CN | 6.8–7.6 | 12 | 6 | 1 |
| 33 | TB | A + P + C | TMS | DN | G | 6.8–7.6 | 12 | 6 | 1 |
| 34 | TB | A + P + C | DMF | NE | OD | 6.8–7.6 | 12 | 6 | 1 |
| 35 | TB | A + P + C | DMAC | NP | AAP | 6.8–7.6 | 12 | 6 | 1 |
| 36 | PB | A + P + C | DMSO | 8HQ HS | ABTS | 6.8–7.6 | 3 | 1 | ½ |
| 37 | PB | A + P + C | DMSO2 | DNS | CN | 6.8–7.6 | 12 | 6 | 1 |
| 38 | PB | A + P + C | TMS | DN | G | 6.8–7.6 | 12 | 6 | 1 |
| 39 | PB | A + P + NAA | DMF | NE | OD | 6.8–7.6 | 12 | 6 | 1 |
| 40 | PB | A + P + C | DMAC | NP | AAP | 6.8–7.6 | 12 | 6 | 1 |
| 41 | PB | A + P + C | DMSO | 8HQ HS | ABTS | 6.8–7.6 | 3 | 1 | ½ |
| 42 | PB | A + P + C | DMSO2 | DNS | CN | 6.8–7.6 | 12 | 6 | 1 |
| 43 | PB | A + P + C | TMS | DN | G | 6.8–7.6 | 12 | 6 | 1 |
| 44 | PB | A + P + C | DMF | NE | OD | 6.8–7.6 | 12 | 6 | 1 |
| 45 | PB | A + P + C | DMAC | NP | AAP | 6.8–7.6 | 12 | 6 | 1 |
| 46 | AB | A + P + C | DMSO | 8HQ HS | TMBd .2H2O | 5.0–6.0 | 12 | 6 | 1 |
| 47 | PB | A + P + C | DMSO2 | DNS | BZ | 6.8–7.6 | 3 | 1 | ½ |
| 48 | PB | A + P + C | TMS | DN | DMB | 6.8–7.6 | 3 | 1 | ½ |
| 49 | AB | A + P + C | DMF | NE | TMB | 5.6–6.0 | 12 | 6 | 1 |
| 50 | AB | A + P + C | DMAC | NP | TMBd | 5.0–6.0 | 12 | 6 | 1 |
| 51 | DW | A + P + C | DMSO | 8HQ HS | TMDd | 5.0–6.0 | 12 | 6 | 1 |
| 52 | DW | A + P + C | DMSO2 | DNS | CN | 6.8–7.6 | 12 | 6 | 1 |
| 53 | DW | A + P + C | TMS | DN | G | 6.8–7.6 | 12 | 6 | 1 |
| 54 | DW | A + P + C | DMF | NE | OD | 6.8–7.6 | 12 | 6 | 1 |
| 55 | DW | A + P + C | DMAC | NP | AAP | 6.8–7.6 | 12 | 6 | 1 |
| 56 | TW | A + P + C | DMSO | 8HQ HS | TMBd | 5.0–6.0 | 12 | 6 | 1 |
| 57 | TW | A + P + C | DMSO2 | DNS | CN | 6.8–7.6 | 12 | 6 | 1 |
| 58 | TW | A + P + C | TMS | DN | G | 6.8–7.6 | 12 | 6 | 1 |
| 59 | TW | A + P + C | DMF | NE | OD | 6.8–7.6 | 12 | 6 | 1 |
| 60 | TW | A + P + C | DMAC | NP | AAP | 6.8–7.6 | 12 | 6 | 1 |
| 61 | AB | A + P + C | DMSO | PQD | AAP | 5.0–6.0 | 12 | 6 | 1 |
| 62 | AB | A + P + C | DMSO | HBP | AAP | 5.0–6.0 | 12 | 6 | 1 |
| 63 | AB | A + P + C | DMSO | DPA | AAP | 5.0–6.0 | 12 | 6 | 1 |
| 64 | AB | A + P + C | DMSO | GSA | TMB | 5.0–6.0 | 12 | 6 | 1 |
| 65 | AB | A + P + C | DMSO | VAA | ABTS | 5.0–6.0 | 12 | 6 | 1 |
| 66 | AB | A + P + C | DMSO | GSA | ABTS | 5.0–6.0 | 12 | 6 | 1 |
| 67 | AB | A + P + C | DMSO | RT | ABTS | 5.0–6.0 | 12 | 6 | 1 |
| 68 | AB | A + P + C | DMSO | 8HQ HS | TMB | 5.0–6.0 | 12 | 6 | 1 |
| 69 | AB | A + P + C | DMSO | VAA | TMB | 5.0–6.0 | 12 | 6 | 1 |
| 70 | AB | A + P + C | DMSO | HDPH | TMB | 5.0–6.0 | 12 | 6 | 1 |
| 71 | PB | A + P + C | DMSO | BMA+ BBA + BA | oPD | 6.8–7.6 | 12 | 6 | 1 |
| 72(a) | PB | A + P + C | DMSO | BMA+ BBA + BA | TPH | 6.8–7.6 | 12 | 6 | 1 |
| 73 | PB | A + P + C | DMSO | NE | ASA | 6.8–7.6 | 12 | 6 | 1 |
| 74 | PB | A + P + C | DMSO | HPB + HPH + HBP | oPD | 6.8–7.6 | 12 | 6 | 1 |
| 75 | PB | A + P + C | DMSO | HPB + HBH + HBP | ASA | 6.8–7.6 | 12 | 6 | 1 |
| 76 | PB | A + P + C | DMSO | HPB + HBH + HBP | AAP | 6.8–7.6 | 12 | 6 | 1 |
| 77 | PB | A + P + C | DMSO | BMA + BBA + BA | ASA | 6.8–7.6 | 12 | 6 | 1 |
| 78(a) | PB | A + P + C | DMSO | HPB + HBH + HBP | TPH | 6.8–7.6 | 12 | 6 | 1 |
| 79 | PB | A + P + C | DMSO | AP + APM + | AEC | 6.8–7.6 | 12 | 6 | 1 |

TABLE VI-continued

Compositions and Stabiltiy Test

| n. | Ag. Solv. | Chel. | Org. Solv. | Cmpd. | Chr. | pH rg. | Shelf life 4° | 25° | 37° |
|---|---|---|---|---|---|---|---|---|---|
| 80 | AB | A + P + C | DMSO | AHHP + DAA AP + APM | AEC | 5.0–6.0 | 12 | 6 | 1 |
| 81 | PB | A + P + C | DMF | AHHP + DAA NE | AEC | 6.8–7.6 | 12 | 6 | 1 |
| 82 | PB | A + P + C | DMF | HPB + HBH + HBP | AEC | 6.8–7.6 | 12 | 6 | 1 |
| 83 | PB | A + P + C | DMF | C8HQ + DPD | AEC | 6.8–7.6 | 12 | 6 | 1 |
| 84(a) | PB | A + P + C | DMSO | BMA + BBA + BA | pPDA | 6.8–7.6 | 12 | 6 | 1 |
| 85(a) | PB | A + P + C | DMSO | GSA | SGD | 6.8–7.6 | 12 | 6 | 1 |
| 86(b) | TB | A + P + C + 8HQ | TMS | DN | OD | 6.8–7.6 | 12 | 6 | 1 |
| 87(b) | BB | A + P + 8HQ | DMSO | 8HQ HS | CN | 7.5–8.5 | 12 | 6 | 1 |
| 88(b) | BB | A + P + C | DMAC | NP | ABTS | 7.5–8.5 | 3 | 1 | ½ |
| 89(b) | DW | A + P + C | DMF | NE | AAP | 6.8–7.6 | 12 | 6 | 1 |
| 90(b) | TW | A + P + C | DMAC | NP | TMBd | 5.0–6.0 | 12 | 6 | 1 |
| 91(b) | BB | A + P + C | DMSO2 | DNS | CN | 7.5–8.5 | 12 | 6 | 1 |
| 92(b) | PB | A + P + C | DMSO | 8HQ HS | ABTS | 6.8–7.6 | 3 | 1 | ½ |
| 93(b) | DW | A + P + C | DMF | NE | OD | 6.8–7.6 | 12 | 6 | 1 |
| 94(a) | TB | A + P + C | DMF | NE | AAP | 6.8–7.6 | 3 | 1 | ½ |
| 95(a) | PB | A + P + C | DMSO2 | DNS | G | 6.8–7.6 | 12 | 6 | 1 |
| 96(a) | AB | A + P + C | DMAC | NP | TMBd. 2H2O | 5.0–6.0 | 12 | 6 | 1 |
| 97(a) | PB | A + P + C | DMF | NE | OD | 6.8–7.6 | 12 | 6 | 1 |
| 98(a) | TW | A + P + C | DMSO2 | DNS | CN | 6.8–7.6 | 12 | 6 | 1 |
| 99(a) | PB | A + P + C | DMF | HPB + HBH + HBP | AEC | 6.8–7.6 | 12 | 6 | 1 |
| 100 | PB | A + P + C | DMSO | 8HQ HS | TMB + CN | 6.8–7.6 | 12 | 6 | 1 |
| 101 | AB | A + C + 8HQ | TMS | DN | TMB + ASA | 5.0–6.0 | 12 | 6 | 1 |
| 102 | PB | A + P + C | DMSO | NE | ASA + AAP | 6.8–7.6 | 12 | 6 | 1 |
| 103 | AB | A + P + C | DMSO | DPA | AAP + CN | 5.0–6.0 | 12 | 6 | 1 |
| 104 | PB | A + P + C | DMSO | NE | ASA + CN | 6.8–7.6 | 12 | 6 | 1 |

Peroxide:
(a) Cumene Hydroperoxide
(b) Absence of peroxide

EXAMPLE 106

Preparation of stable solution containing o-dianisidine:

(a) 50 mg of citric acid tri-sodium salt, 5 mg of acetanilide and 5 mg of sodium pyrophosphate decahydrate were dissolved in 80 ml of Tris buffer 0.001M, having a pH of 7.2.

(b) 10 mg of 8-hydroxyquinoline, 100 mg of 2,3-dinitro-1-naphthol-7 sulfonic acid, and 20 mg of o-dianisidine were dissolved in 20 ml of sulfolane.

Solutions (a) and (b) were mixed and titrated to obtain a pH of 7.2. 10 Microliters of $H_2O_2$ were added to the resulting solution.

The solution had a shelf-life of 12 months at 4° C., 6 months at 25° C. and one month at 37° C.

EXAMPLE 107

Preparation of stable solution containing 4-aminoantipyrine/alpha-naphthol.

(a) 50 mg of citric acid tri-sodium salt, 5 mg of acetanilide and 5 mg of sodium pyrophosphate decahydrate were added to 75 ml of phosphate buffer 0.001M, having a pH of 7.6.

(b) 100 mg of 8-hydroxyquinoline hemi-sulfate salt, 50 mg of 4-aminoantipyrine and 500 mg of alpha-naphthol were dissolved in 25 ml of N,N-dimethylacetamide.

Solutions (a) and (b) were mixed and NaOH 0.1N was added, to obtain a pH of 6.9, together with 10 microliters of $H_2O_2$. The shelf-life of the resulting solution was as in Example 62.

EXAMPLE 108

Preparation of stable solution containing 4-aminoantipyrine/phenol.

Example 63 was repeated but using 500 mg of phenol instead of alpha-naphthol. The results were as in Example 63.

EXAMPLE 109

Preparation of stable solution containing 2,4-dichloro-1-naphthol.

(a) 40 mg of citric acid tri-sodium salt, 8 mg of acetanilide and 8 mg of sodium pyrophosphate decahydrate were dissolved in 50 ml of distilled water.

(b) 50 mg of 2,4-dinitro-1-naphthol and 25 mg of 3,3',5,5'-tetramethylbenzidine.2HCL.2H2O were dissolved in 50 ml of dimethylsulfone, soluted in DW.

Solutions (a) and (b) were mixed and brought to a pH of 5.0. 10 microliters of $H_2O_2$ were added. The stability results obtained were as in the previous example.

EXAMPLE 110

(a) 40 mg of citric acid tri-sodium salt, 4 mg of acetanilide and 4 mg of sodium pyrophosphate were dissolved in 60 ml of tap water.

(b) 10 mg of 8-hydroxyquinoline, 50 mg of guaiacol and 100 mg of 8-hydroxyquinoline hemi-sulfate salt were dissolved in 40 ml of DMSO.

Compositions (a) and (b) were mixed together and with 10 microliters of $H_2O_2$. The pH of the resulting composition was brought to 7.0. Shelf lives of not less than 12, 6 and 1 months for 4°, 25° and 37° C., respectively, were obtained.

EXAMPLE 111

(a) 7 mg of acetanilide, 5 mg of sodium pyrophosphate and 15 mg of citric acid tri-sodium salt were dissolved in 90 ml of phosphate buffer.

(b) 20 mg of trioxane were completely dissolved in the above solution.

(c) 100 mg of chloronaphthol and 200 mg of 8-hydroxyquinoline were then dissolved in the above solution, which was then titrated to obtain a pH of 7.2-7.4.

(d) 100 microliters of $H_2O_2$ (30% aqueous solution) were then added.

Shelf lives were obtained as in the preceding example.

EXAMPLE 112

A solution is prepared which contains 100 mg aminoethylcarbazole in 30 ml dimethylformamide, 100 mg 2-amino-4-picoline, acetate buffer (0.01M, pH 5.0, 70 ml), containing sodium pyrophosphate (100 mg), sodium citrate (100 mg) and acetanilide (100 mg), and 30 μl $H_2O_2$. The solution obtained shows a stability of 1 month at 37° C., 6 months at 25° C., and 12 months at 4° C.

EXAMPLE 113

The solution is prepared as in Example 112 above but using 100 μl 2-butanone peroxide instead of $H_2O_2$. Shelf lives obtained as in Example 112.

EXAMPLE 114

A solution is prepared containing a 100 mg o-phenylenediamine in 30 ml dimethylsulfoxide, 100 mg 2-amino-4-picoline, phosphate buffer (0.01M, pH 7.2 70 ml) containing 100 mg sodium pyrphosphate, 100 mg sodium citrate and 100 mg acetanilide, and 100 μl $H_2O_2$. The shelf life of the obtained solution is 3 weeks at 37° C., 2 months at 25° C. and 12 months at 4° C.

EXAMPLE 115

A solution is prepared containing 100 mg tetramethylbenzidine in 40 ml dimethylsulfoxide, 1 g 2,4,6-collidine, acetate buffer (60 ml, 0.01M, pH 4.0) containing 50 mg sodium pyrophosphate, 50 mg sodium citrate and 50 mg acetanelide, and 100 μl 2-butanone peroxide. Shelf lives obtained as in Example 114.

EXAMPLES 116 and 117

Example 115 is repeated using 100 μl cumene hydroperoxide and 100 μl tert-butylhydroperoxide as the peroxides. Shelf lives obtained in each case as in Example 112.

EXAMPLE 118

A solution of 100 mg 4-chloro-1-naphthol in 30 ml DMSO is prepared, to which it is added 1 g guaiacol sulfonic acid, phosphate buffer (70 ml, 0.05M, pH 7.4) containing 50 mg sodium pyrophosphate, 50 mg sodium citrate and 50 mg acetanilide, and 50 μl $H_2O_2$. Shelf life is 1 month at 37° C., 6 months at 25° C. and 12 months at 4° C.

EXAMPLE 119

Example 118 is repeated but using 2,6-lutidin instead of guaiacol sulfonic acid. Shelf lives obtained as in Example 118.

EXAMPLE 120

A solution is prepared using 100 mg tetramethylbenzydine as the chromogen material in 30 ml DMSO and in 10 g citric acid (soluted in 70 ml distilled water) as the solvent. There are added 60 mg sodium pyrophosphate, 60 mg acetanilide, 60 mg sodium citrate, 60 mg 8-hydoxyquinoline and 100 μl Cumene hydroperoxide. The resulting pH of the solution is 2. Shelf lives are 1 month at 37° C., 6 months at 25° C. and 12 months at 4° C.

EXAMPLE 121

4-Chloro-1-naphthol (100 mg in 30 ml DMSO) is soluted in a carbonate buffer (70 ml, 0.02M, pH 9.0). Sodium pyrophasphate (50 mg), acetanilide (50 mg), sodium citrate (50 mg) and 8-hydroxyquinoline (50 mg) are added, and further it is added 50 μl $H_2O_2$. Shelf lives obtained as in Example 120.

The above examples have been given for the purpose of illustration and are not intended to be limitative. Many variations can be provided in the various chemical compounds, compositions and methods described, without exceeding the scope of the invention.

I claim:

1. A stable liquid composition containing a chromogen material and hydrogen peroxide, consisting essentially of an aqueous solvent medium, a chromogenic material, hydrogen peroxide, a water miscible organic solvent, a stabilizing unsaturated nitrogen heterocyclic compound and an effective amount of a chelating agent to stabilize said chromogen and hydrogen peroxide containing composition in its liquid state, said aqueous solvent medium being present in sufficient amount to provide a stable liquid composition containing at least 50% water by volume.

2. The stable chromogen and hydrogen peroxide containing composition of claim 1, wherein said stabilizing compound is selected from the group consisting of compounds having the general formula:

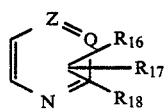

wherein each of Z and Q is either C or N, but both Z and Q are not N, each of $R_{16}$, $R_{17}$, and $R_{18}$ is independently selected from the group consisting of hydrogen, hydroxy, —NH, alkyl, amino, —$SO_3H$, —$CO_2H$, benzo, piperidino, pyrrolidino, substituted pyrrolidino, and an isoimidizole substituent; and
salts of such compounds.

3. The stable chromogen and hydrogen peroxide containing composition of claims 1 or 2, having a pH of between about 2 and 5.

4. The stable chromogen and hydrogen peroxide containing composition of claims 1 or 2, having a pH of between about 7 and 11.

5. The stable chromogen and hydrogen peroxide containing composition of claim 2, wherein said stabilizing compound is selected from among the group consisting of 2-amino-4,6-diemthylpyridine, 2-amino-4,6-dimethylpyrimidine, 2-amino-6-methyl pyridine, 2,4,6-collidine, 3-(aminomethyl) pyridine, 2-quinoxalinol, 4-amino-2,6-dimethylpyridine, 5-ethyl-2-methylpyridine, 4-methylpyrimidine, 2,6-lutidin, ethyl nicotinate, 4-piperidinopyridine, 2-aminoethylpyridine, 4-pyridinecarboxylic acid, pyridine-3-sulfonic acid and purine.

6. The stable chromogen and hydrogen peroxide containing composition of claim 2, wherein said aqueous solvent medium contains a buffer solution selected from the group consisting of phosphate buffer, Tris buffer(hydroxymethyl-aminomethane), borate buffer, glycine buffer and acetate buffer.

7. The stable chromogen and hydrogen peroxide containing composition of claim 1, wherein said water miscible organic solvent has a gas-phase dipole moment of at least about 1.60 D.

8. The stable chromogen and hydrogen peroxide containing composition of claim 7, wherein said water miscible organic solvent has a gas-phase dipole moment of at least about 1.69 D.

9. The stable chromogen and hydrogen peroxide containing composition of claim 1, wherein said water miscible organic solvent contains an aprotic solvent.

10. The stable chromogen and hydrogen peroxide containing composition of claim 1, wherein said chromogenic material is selected from the group consisting of chloronaphthol, benzidine, tetramethylbenzidine, 3-amino-9-ethylcarbazole, dichloronaphthol, dibromonaphthol, 3,3',5,5'-tetramethylbenzidine dihydrochloride, 3,3',5,5'-tetramethylbenzidine dihydrate, 3,3',5,5'-tetramethylbenzidine dihydrochloride dihydrate, 3-methylbenzothiazole-2,1-hydrazone, parahydroxyphenyl acetic acid, 2,2'-azino-di (3-ethylbenzothiazoline) sulfonic acid, 4-aminoantipyrin/alpha-naphthol, o-dianizidine, o-toluidine, 5-amino salicilic acid, guaiacol, o-tolidine and pyrogallol.

11. The stable chromogen and hydrogen peroxide containing composition of claim 1, wherein said aqueous solvent medium contains a buffer solution.

12. The stable chromogen and hydrogen peroxide containing composition of claim 1, wherein said chelating agent is selected from the group consisting of pyrophosphate, nitrilotriacetic acid, acetanilide, citrate, a derivative of 8-hydroxyquinoline and mixtures thereof.

13. The stable chromogen and hydrogen peroxide containing composition of claim 12, wherein said chelating agent contains up to about 200 ppm of said pyrophosphate, up to about 200 ppm of said acetanilide, up to about 1000 ppm of said citrate, and up to about 50 ppm of said 8-hydroxyquinoline or a salt thereof.

14. The stable chromogen and hydrogen peroxide containing composition of claim 1, wherein said water miscible organic solvent is selected from the group consisting of methanol, ethanol, dioxane, dimethylsulfoxide, sulfolane, acetamide, soluted dimethylsulfone, hexamethylphosphoric triamide, N-methylacetamide, dioxane, dimethylformamide, soluted trioxane, formamide and tetrahydrofuran.

* * * * *